United States Patent
Ko et al.

(10) Patent No.: US 7,053,131 B2
(45) Date of Patent: May 30, 2006

(54) ABSORBENT ARTICLES COMPRISING SUPERCRITICAL FLUID TREATED HIPE, I-HIPE FOAMS AND OTHER FOAMS

(75) Inventors: Young C. Ko, Neenah, WI (US); Jeffrey D. Lindsay, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 516 days.

(21) Appl. No.: 10/308,938

(22) Filed: Dec. 3, 2002

(65) Prior Publication Data

US 2003/0134918 A1 Jul. 17, 2003

Related U.S. Application Data

(63) Continuation of application No. 09/966,282, filed on Sep. 28, 2001, now Pat. No. 6,525,019, which is a continuation-in-part of application No. PCT/US99/19026, filed on Aug. 20, 1999.

(60) Provisional application No. 60/097,395, filed on Aug. 21, 1998.

(51) Int. Cl.
*C08J 9/28* (2006.01)
*A61F 13/15* (2006.01)

(52) U.S. Cl. .......................... 521/50.5; 521/64; 521/65; 521/72; 604/358; 604/369

(58) Field of Classification Search ................. 521/50.5, 521/64, 65, 72; 604/358, 369
See application file for complete search history.

(56) References Cited

U.S. PATENT DOCUMENTS

| | | | |
|---|---|---|---|
| 3,901,236 A | | 8/1975 | Assarsson et al. |
| 5,002,814 A | | 3/1991 | Knack et al. |
| 5,128,382 A | | 7/1992 | Elliott et al. |
| 5,147,343 A | | 9/1992 | Kellenberger |
| 5,260,345 A | | 11/1993 | DesMarais et al. |
| 5,268,224 A | | 12/1993 | DesMarais et al. |
| 5,331,015 A | | 7/1994 | DesMarais et al. |
| 5,358,046 A | | 10/1994 | Sydansk et al. |
| 5,397,316 A | | 3/1995 | LaVon et al. |
| 5,422,377 A | * | 6/1995 | Aubert ............... 521/64 |
| 5,436,066 A | | 7/1995 | Chen |
| 5,443,760 A | | 8/1995 | Kasprzak |
| 5,489,469 A | | 2/1996 | Kobayashi et al. |
| 5,629,353 A | * | 5/1997 | Steckle et al. ............. 521/64 |
| 5,652,194 A | | 7/1997 | Dyer et al. |
| 5,672,667 A | | 9/1997 | Desimone et al. |
| 5,710,187 A | * | 1/1998 | Steckle et al. ............. 521/64 |
| 5,733,964 A | | 3/1998 | Johnston et al. |
| 5,800,418 A | | 9/1998 | Ahr |
| 5,817,704 A | | 10/1998 | Shiveley et al. |
| 6,187,828 B1 | | 2/2001 | Woodrum et al. |
| 6,261,679 B1 | | 7/2001 | Chen et al. |
| 6,278,037 B1 | | 8/2001 | Schmidt et al. |
| 6,299,808 B1 | | 10/2001 | Mork et al. |
| 6,369,121 B1 | | 4/2002 | Catalfamo et al. |
| 6,486,379 B1 | | 11/2002 | Chen et al. |
| 2002/0053754 A1 | | 5/2002 | Katoh et al. |
| 2003/0012928 A1 | | 1/2003 | Malowaniec et al. |
| 2003/0093051 A1 | | 5/2003 | Malowaniec et al. |

FOREIGN PATENT DOCUMENTS

| | | |
|---|---|---|
| EP | 0 478 150 A2 | 4/1992 |
| EP | 0 478 150 B1 | 11/1998 |
| EP | 1 038 573 A2 | 9/2000 |
| WO | WO 90/11181 A1 | 10/1990 |
| WO | WO 99/26670 A1 | 6/1999 |
| WO | WO 00/53639 A1 | 9/2000 |
| WO | WO 01/26595 A1 | 4/2001 |
| WO | WO 01/64153 A1 | 9/2001 |
| WO | WO 01/64154 A1 | 9/2001 |

OTHER PUBLICATIONS

American Society for Testing Materials (ASTM) Designation: D 3574–86, "Standard Methods of Testing Flexible Cellular Materials—Slab, Bonded, and Molded Urethane Foams," published May 1986.

Butler, Rachel et al., "Emulsion Templating Using Supercritical Fluid Emulsions," *Polymer Reprints*, vol. 43, No. 1, Spring 2002, pp. 744–745.

Cooper, Andrew, "Materials HIPE Creating Nanostructures Using SCFs," *Material World*, vol. 10, No. 1, Jan. 2002, pp. 24–26.

Dong, Xing et al., "Phase Behavior and Micelle Size of an Aqueous Microdispersion in Supercritical CO2 With a Novel Surfactant," Industrial & Engineering Chemistry Research, vol. 41, No.5, 2002, pp. 1038–1042.

Harrison, Kristi et al., "Water–in Carbon Dioxide Microemulsions With a Fluorocarbon–Hydrocarbon Hybrid Surfactant," *Langmuir*, vol. 10, No. 10, 1994, pp. 3536–3541.

Hoefling, T.A. et al., "Design and Synthesis of Highly Carbon Dioxide–Soluble Surfactants and Chelating Agents," Fluid Phase Equilibria, vol. 83, 1993, pp. 203–212.

American Society for Testing Materials (ASTM) Designation: D3574–86, "Standard Methods of Testing Flexible Cellular Materials—Slab, Bonded, and Molded Urethane Foams," published May 1986.

Butler, Rachel et al., "Emulsion Templating Using Supercritical Fluid Emulsions," *Polymer Reprints*, vol. 43, No. 1, Spring 2002, pp. 744–745.

Cooper, Andrew, "Materials HIPE Creating Nanostructures Using SCFs," *Material World*, vol. 10, No. 1, Jan. 2002, pp. 24–26.

(Continued)

*Primary Examiner*—Morton Foelak
(74) *Attorney, Agent, or Firm*—Bryan R. Rosiejka

(57) ABSTRACT

The present invention comprises compositions and methods of making high internal phase emulsion foam (HIPE) and inverse high internal phase emulsion foam (I-HIPE) using super critical fluids. Such foams may be used in a wide variety of articles such as absorbent articles.

22 Claims, No Drawings

OTHER PUBLICATIONS

Dong, Xing et al., "Phase Behavior and Micelle Size of an Aqueous Microdispersion in Supercritical CO2 With a Novel Surfactant," Industrial & Engineering Chemistry Research, vol. 41, No. 5, 2002, pp. 1038–1042.

Harrison, Kristi et al., "Water–in Carbon Dioxide Microemulsions With a Fluorocarbon–Hydrocarbon Hybrid Surfactant," Langmuir, vol. 10, No. 10, 1994, pp. 3536–3541.

Hoefling, T.A. et al., "Design and Synthesis of Highly Carbon Dioxide–Soluble Surfactants and Chelating Agents," Fluid Phase Equilibria, vol. 83, 1993, pp. 203–212.

Johnston, Keith P. et al., "Microemulsions, Emulsions and Lataxes," Chemical Synthesis Using Supercritical Fluids, ed. P.G. Jessop and W. Leitner, Wiley–VCH Verlag GmbH, 1999, pp. 127–146.

Lee, C. Ted et al., "Water–in–Carbon Dioxide Emulsions: Formation and Stability," Langmuir, vol. 15, No. 20, 1999, pp. 6781–6791.

Liu, Juncheng et al., "Investigation of Nonionic Surfactant Dynol–604 Based Reverse Microemulsions Formed in Supercritical Carbon Dioxide," Langmuir, vol. 17, No. 26, 2001, pp. 8040–8043.

Liu, Juncheng et al., "Formation of Water–in–CO2 Microemulsions With Non–Fluorous Surfactants Ls–54 and Solubilization of Blomacromolecules," Chemistry—A European Journal, vol. 8, No. 6, 2002, pp. 1356–1360.

Neumann, A.W., and R.J. Good, "Techniques of Measuring Contact Angles," Chapter 2 of Surface and Colloid Science, vol. 11, Experimental Methods, edited by R.J. Good and R.R. Stromberg, Plenum Press, 1979, pp. 31–91.

O'Neill, Mark L. et al., "Polymer Stabilized Emulsions in Supercritical Carbon Dioxide," Polymeric Matererials Science and Engineering, vol. 74, Proceedings of the American Chemical Society, Spring Meeting, New Orleans, LA, 1996, pp. 228–229.

O'Neill, Mark L. et al., "Dispersion Polymerization in Supercritical CO2 With Siloxane–Based Macromonomer. 2. The Particle Formation Regime," Macromolecules, vol. 31, No. 9, 1998, pp. 2848–2858.

Shutov, Dr. Fyodor A., "Syntactic Polymer Foams," Chapter 16, Handbook of Polymeric Foams and Foam Technology, Hanser Publishers, Oxford University Press, New York, 1991, pp. 355–359.

"Supercritical Carbon Dioxide/Water Emulsion Found Effective for Remediating Metal Contaminants in Waste," Internet web page "http://www.lanl.gov/worldview/news/releases/archive/02–030.shtml", Los Alamos National Laboratory, viewed and printed on Aug. 5, 2002, pp. 1–4.

Yazdi, A.V. et al., "Highly Carbon Dioxide Soluble Surfactants, Dispersants and Chelating Agents," Fluid Phase Equilibria, vol. 117, Nos. 1–2, 1996, pp. 297–303.

Patent Cooperation Treaty Search Report from the International Search Authority, International Application No. PCT/US 03/29848 dated Apr. 28, 2004.

* cited by examiner

ABSORBENT ARTICLES COMPRISING SUPERCRITICAL FLUID TREATED HIPE, I-HIPE FOAMS AND OTHER FOAMS

FIELD OF THE INVENTION

The present invention is directed to absorbent composites having enhanced intake rates and retention properties. The present invention is also directed to a method of making absorbent composites having enhanced intake rates and retention properties. The present invention is further directed to compositions comprising the absorbent composites.

BACKGROUND OF THE INVENTION

In the manufacture of highly absorbent materials and structures for use in personal care products such as diapers, feminine hygiene products and bandages, there is a continual effort to improve performance characteristics. Although the structure of these personal care products have many components, in many instances the in-use performance of the product is directly related to the characteristics of the absorbent composite it contains. Accordingly, manufacturers of these products strive to find ways of improving the properties of the absorbent composite in order to reduce leakage while providing comfort to a wearer.

One means of reducing the leakage and increasing absorbency has been the extensive use of superabsorbent materials. Recent trends in commercial diaper design have been to use more superabsorbent materials and less fiber in order to make the product thinner. However, products with a high content of superabsorbent materials still leak, as many absorbent materials are unable to absorb a liquid at the rate at which the liquid is applied to the absorbent composite during use. The addition of fibrous material to the absorbent composite decreases the amount of leakage of an absorbent composite by temporarily holding the liquid until the superabsorbent material absorbs it. Fibers also serve to separate the particles of superabsorbent material to avoid or reduce gel-blocking. As used herein, the term "gel-blocking" refers to a situation wherein particles of superabsorbent material deform during swelling and block the interstitial spaces between the particles, or between the particles and the fibers, thus preventing the flow of liquid through the interstitial spaces. Even when fibrous material is incorporated into an absorbent composite, a poor choice of a superabsorbent material, especially one which exhibits gel-blocking behavior within the absorbent composite, results in poor liquid handling properties in the life cycle of the absorbent composite. Consequently, the choice of absorbent composite materials greatly affects the in-use absorbency and leakage of the absorbent product. To reduce leakage during the life cycle of the product, it is desirable to maintain the level of intake performance of the absorbent composite throughout the life of the product.

Polymeric foams, such as those described in U.S. Pat. No. 5,397,316 to LaVon et al., have many advantages in absorbent products. High internal phase emulsion foams (HIPE), such as those described in U.S. Pat. No. 5,331,015, have been developed in an effort to create absorbent polymeric foams with enhanced fluid intake. These HIPE foams are prepared by polymerizing water-in-oil emulsions having a relatively small amount of an oil phase and a relatively greater amount of a water phase. However, this type of HIPE foam is expensive and has poor wettability and no swelling capability thereby creating problems with its use as a superabsorbent composite. Additionally inverse HIPE (I-HIPE) foams have been developed using oil-in-water (O/W) emulsion systems. However, there has been difficulty in extracting the oil phase that may be entrapped by the polymer matrix after polymerization.

What is needed is an absorbent composite having improved composite properties. What is also needed is an absorbent composite, capable of mass production which exhibits an improved fluid intake rate, and/or fluid intake of multiple insults over the life of the composite.

SUMMARY OF THE INVENTION

The present invention comprises compositions and methods of making absorbent polymeric foams using super critical fluid technology. The super critical fluid technology can be used in both traditional high internal phase emulsion foams (HIPE) and inverse high internal phase emulsion foam (I-HIPE) technology. The present invention further comprises a method for making an absorbent composite capable of cost effective mass production without the problems associated with known absorbent composites. The present invention additionally comprises articles comprising the absorbent composite.

Traditional High Internal Phase Emulsion foams (HIPE), particularly water-in-oil emulsion systems, have been proposed for many uses, including absorbent articles. The monomer and crosslinking agents are present in the oil phase, while an electrolyte can be present in the water phase in water-in-oil (W/O) emulsion systems. Subsequent removal of the aqueous liquid remaining in the foam requires pressing, thermal drying, or vacuum dewatering. Inverse HIPE foams such as oil-in-water (O/W) emulsion systems have suffered from the difficulty of extracting the oil phase in the polymer matrix after polymerization. With supercritical fluid technology enabling the replacement of the oils with supercritical fluids that are non-toxic, environmentally friendly, more soluble and have little or no interaction with the foaming material, it is possible to create cost effective polymeric foams capable of mass production which exhibit improved fluid intake rate, and superior fluid intake of multiple insults over the life of the composite, without the problems associated with known absorbent composites.

DETAILED DISCLOSURE OF THE INVENTION

The present invention comprises compositions and methods of making absorbent polymeric foams using super critical fluids. Super critical fluids, such as $CO_2$, are substituted either completely or partially for the oil of an oil-in-water HIPE or in the water-in-oil emulsion of an inverse HIPE system. After polymerization in the water phase occurs, the $CO_2$ is easily extracted from the polymer as a gas. Super critical fluid processing can be used in the manufacture of existing foams, such as HIPE foams, I-HIPE foams or polyolefin foams, wherein, for example, the supercritical $CO_2$ causes swelling of the polymeric matrix, allowing diffusion of surface active agents or other active components into the matrix in the swollen state, wherein upon depressurization, the matrix deswells and entraps the active components in the outer layers of the matrix to modify the surface chemistry and other properties of the foam. By controlling the nature of the emulsion, and the polymerization process, nanopores can be created or very large gradient pores can be created such that one side of a foam sheet has large pores for good intake, while the opposing side has extremely small pores for high capillary pressure and retention.

The use of supercritical fluids in emulsions is described in "Materials HIPE creating nanostructures using SCFs", Material World, Vol. 10 (no. 1), January 2002, pp. 24–26, and in "Emulsion Templating Using Supercritical Fluid Emulsions" by Rachel Butler, Cait M. Davies, Ian Hopkinson, and Andrew I. Cooper, Polymer Preprints, Vol. 42, No. 1, 2002, pp. 744–745, (Butler et al.), all of which are herein incorporated by reference. Such technologies can be adapted to improve known HIPE polymerization processes used in the production of foams for absorbent articles, particularly by using supercritical carbon dioxide or other supercritical fluids to replace the oil phase in the HIPE foam-production process to generate foams having higher capillary tension or other improved physical and interfacial properties relative to past HIPE foams.

The present invention further comprises a method for making an absorbent composite capable of cost effective mass production which has improved fluid intake over multiple insults. The compositions of the present invention further comprise superabsorbent polymeric foam produced by inverse high internal phase emulsion (I-HIPE) and HIPE polymerization of in-situ redox monomers for use in absorbent personal care articles such as diapers, feminine hygiene products such as sanitary napkins or tampons, disposable training pants, incontinence devices, medical sponges, cleaning articles such as sponges joined to abrasive layers, numerous other articles for absorbing body fluids or other fluids, and bandages or wound dressings. In some embodiments, a HIPE or I-HIPE foam material processed with supercritical fluid as the carrier in the oil phase is used as a hydrophilic component of an absorbent core intended for receiving and storing body fluids such as urine, menses, blood, sweat, and the like. The absorbent article may comprise a liquid-permeable topsheet that is placed next to the body, an absorbent core comprising a foam produced with supercritical fluid as the carrier in the oil phase of a HIPE or I-HIPE process, and a backsheet, such that the absorbent core is sandwiched between the topsheet and the backsheet. Exemplary absorbent articles into which a supercritical-fluid-processed foam layer can be included are disclosed, by way of example only, in U.S. Pat. No. 6,486,379, "Absorbent Article with Central Pledget and Deformation Control," issued Nov. 26, 2002 to Chen et al., herein incorporated by reference.

Definitions

As used herein, "foams" are two-phase gas-solid systems that have a supporting solid lattice of cell walls that are continuous throughout the structure. The gas (typically air) phase in a foam is usually distributed in void pockets often called cells. "Open-celled foams" are polymeric materials having substantial void space in the form of cells defined by a plurality of mutually connected, three dimensionally branched webs of polymeric material, wherein the cells typically have openings to permit fluid communication from one cell to another. In other words, the individual cells of the foam are for the most part not completely isolated from each other by the polymeric material of the cell walls. Thus, the cells in such substantially open-celled foam structures have intercellular openings or "windows" which are large enough to permit ready fluid transfer from one cell to the other within the foam structure. Many of the open-celled foams useful in the present invention have a reticulated character. The strands of polymeric material which make up the branched webs of the open-celled foam structure are referred to as "struts." Sponge-like materials with interconnected cells are an example of open-celled foams.

For purposes of the present invention, a foam material is "open-celled" if at least 70%, more preferably 80%, most preferably 95% of the cells in the foam structure are at least 1 micron in size and are in fluid communication with at least one adjacent cell. Alternatively, a foam material may be considered to be substantially open-celled if it has a measured available pore volume that is at least 80% of the theoretically available pore volume. In the case of HIPE foams, the theoretically available pore volume may be determined by the water-to-oil weight ratio of the HIPE emulsion from which the foam material is formed. In the case of I-HIPE foams, the available pore volume may be determined by the oil-to-water weight ratio of the I-HIPE emulsion from which the foam material is formed.

"Frazier permeability" is a well-known measure of air permeability measured as standard cubic feet per minute of air flow across a material, per square foot of material with an air pressure differential of 0.5 inches of water (125 Pa) across the sample, as measured with an air permeability test device such as the Frazier 2000™ Differential Pressure Air Permeability device from Frazier Precision Instruments (Hagerstown, Md.). Frazier permeability is simply reported as the "CFM" reading. The sample should be substantially planar for a Frazier permeability test and have a basis weight of about 30 gsm, or may be normalized to a 30 gsm sample. The materials of the present invention, in some embodiments, may have Frazier permeabilities of about 20 cfm or above, more specifically about 50 cfm or above, still more specifically about 100 cfm or above, and most specifically about 200 cfm or above, with an exemplary range of from about 75 cfm to about 1100 cfm.

As used herein, a foam is "flexible" if it meets a modified flexibility test based on the flexibility tests for various foams provided by the American Society for Testing and Materials (ASTM). Specifically, a flexible foam is one that does not rupture when a 20×2.5×2.5 cm piece is wrapped around a 2.5 cm mandrel at a uniform rate of 1 lap/5 seconds at 20 degrees Centigrade. "Rigid" foams are those which rupture in the above-mentioned test. Foam structures of the present invention can be either flexible or rigid, with flexible foams being desirable for some body fit applications in certain absorbent articles.

As used herein, "wet flexibility" is determined by a modified form of the foam flexibility test procedure given in a standard test method of the ASTM known as ASTM D 3574-86, 3.3 test used to determine flexibility of cellular organic polymeric foam products. Such a modified test utilizes a foam sample which is 7×0.8×0.8 cm and which has been saturated to its free absorbent capacity with a commercially available saline solution, such as S/P certified blood bank saline (Stephens Scientific of Riverdale, N.J., distributed by Baxter Healthcare of McGraw Park, Ill., under catalog #B3158-1) at 37° C. It is important that the cutting process used to make these samples does not introduce edge defects in the strip. The saturated foam strip is bent around a 2.5 cm diameter cylindrical mandrel at a uniform rate of 1 lap in 5 seconds. The foam is considered flexible if it does not tear or break during this test, i.e., if it passes one bending cycle, then the material is wet flexible.

As used herein, the term "cellulosic" is meant to include any material having cellulose as a major constituent, and specifically comprising at least 50 percent by weight cellulose or a cellulose derivative. Thus, the term includes cotton, typical wood pulps, cellulose acetate, cellulose triacetate, rayon, thermomechanical wood pulp, chemical wood pulp, debonded chemical wood pulp, milkweed, bacterial cellulose, microfibrillated cellulose, microcrystalline cellulose, regenerated cellulose, lyocell, and the like.

As used herein, the term "in-situ SAP precursor monomer" refers to monomers which are used to produce a water-absorptive polymer and the polymerization of the monomers may be initiated with the use of a redox initiator. Organic unsaturated carboxylic acids or salts are representative of such monomers. Specific examples include acrylic acid or salts thereof, methacrylic acid or salts thereof, maleic acid or salts thereof, and itaconic acids or salts thereof. Generally, water-soluble monomers are used in the I-HIPE process since in-situ polymerization is carried out in the water phase.

As used herein, the term "rubbery monomer" refers to monomeric materials which would exhibit a low glass transition temperature about 40° C. or lower. Monofunctional rubbery co-monomers of this type include, but are not limited to, C4–C12 alkyl-acrylates, the C6–C14 alkylmethacrylates, and combinations of such co-monomers, such as N-butylacrylate and 2-ethylhexylacrylate.

As used herein, the term "hydrophobic" refers to a material having a contact angle of water in air of at least 90 degrees. In contrast, as used herein, the term "hydrophilic" refers to a material having a contact angle of water in air of less than 90 degrees. For the purposes of this application, contact angle measurements are determined as set forth in Robert J. Good and Robert J. Stromberg, Ed., in "Surface and Colloid Science—Experimental Methods," Vol. II (Plenum Press, 1979), herein incorporated by reference. The I-HIPE foams of the present invention are hydrophilic since SAP precursor monomers are used and therefore do not require any subsequent treatment to make them hydrophilic.

As used herein, the term "emulsifier or surfactant" includes a single surfactant or a mixture of two or more surfactants. If a mixture of two or more surfactants is employed, the surfactants may be selected from the same or different classes, provided only that the surfactants present in the mixture are compatible with each other. In general, the surfactant may be any surfactant known to those having ordinary skill in the art, including anionic, cationic, and nonionic surfactants. Examples of anionic surfactants include, among others, linear and branched-chain sodium alkylbenzenesulfonates, linear and branched-chain alkyl sulfates, and linear and branched-chain alkyl ethoxy sulfates. Cationic surfactants include, by way of illustration, tallow and trimethylammonium chloride. Examples of nonionic surfactants, include, again by way of illustration only, alkyl polyethoxylates; polyethoxylated alkylphenols; fatty acid ethanol amides; and complex polymers of ethylene oxide, propylene oxide, alcohols, nonyl phenol polyenthylene oxide adducts; block polymers of ethylene oxide and propylene oxide adducts; block polymers of ethylene oxide and propylene oxide; sorbitan fatty acid esters such as sorbitan monolaurate, sorbitan monomyristylate, sorbitan monopalmitate, sorbitan monostearate, sorbitan tristearate, sorbitan monooleate, sorbitan trioleate, sorbitan sesquioleate, and sorbitan disterate; glycerin fatty acid esters such as glycerol monostearate, glycerol monooleate, diglycerol monooleate, and self emulsifying glycerol monostearate; polyoxyethylene alkyl ethers such as polyoxyethylene lauryl ether, polyoxyethylene cetyl ether, polyoxyethylene stearyl ether, polyoxyethylene oleyl ether, and polyoxyethylene higher alcohol ethers; polyoxyethylene alkylaryl ethers such as polyoxyethylene nonnylphenyl ether; polyoxyethylene sorbitan fatty acid esters such as polyoxyethylene sorbitan monolaurate, polyoxyethylene sorbitan monomyristylate, polyoxyethylene sorbitan monopalmintate, polyoxyethylene sorbitan monostearate, polyoxyethylene sorbitan tristearate, and polyglycol ether sulfate; sodium sulforicinioate; alkyl sulfonates such as sulfonated paraffin salts; sodium dodecyl benzene sulfonate, alkyl sulfonates such as alkali metal sulfates of alkali phenol hydroxyethylene; higher alkyl napthalene sulfonates; fatty acid salts such as naphthalene sulfonic acid formalin condensate, sodium laureate, triethanol amine oleate, and triethanol amine apiate; polyoxyalkyl ether sulfuric esters; sulfuric esters of polyoxyethylene carboxylic ester and polyoxyethylene phenyl ether sulfuric esters; succinic acid dialkyl ester sulfonates; and polyoxy ethylene alkyl aryl sulfates. Silicone polyether surfactants can also be used, particularly when silicone oils or other silicone compounds are present in the oil phase.

As used herein, "cross-linking monomer" means a compound having at least two polymerizing unsaturated groups in the molecular unit. Though the organic unsaturated carboxylic acid or salt thereof, particularly acrylic acid or a salt thereof may undergo self-crosslinked superabsorbent polymer, a crosslinking agent may also be added to crosslink the polymerized material in the oil-in-water type inverse high internal phase emulsion. Typical examples of cross-linking monomers are divinyl compounds copolymerizable with SAP precursor monomers such as N-N'methylenebis (meth)acrylamide and (poly)ethylene glycoldi(meth) acrylate, and water soluble compounds having two or more functional groups reactive with carboxylic acid, for example, polyglycidyl ethers, such as ethylene glycol diglycidyl ether and polyglycidyl ether. When rubbery monomers are added to the oil phase to copolymerize with water-soluble SAP precursor monomers, then unsaturated chemicals such as the following may also be added: divinyl benzene, trivinyl benzene, divinyl toluene, divinyl xylene, p-ethyl-vinylbenzene, divinyl naphthalene, divinyl alkyl benzenes, divinyl phenanthrene, divinyl biphenyl, divinyl diphenylmethane, divinyl benzyl, divinyl phenyl ether, and divinyl diphenyl sulfide; oxygen-containing monomers such as vinyl furan; sulfur-containing monomers such as divinyl sulfide and divinyl sulfone; aliphatic monomers such as butadiene, isoprene, and pentadiene; ethylene glycol diacrylate, ethylene glycol dimethacrylate, 1,3 butane diol diacrylate, 1,3 butane diol dimethacrylate, 1,4 butane diol diacrylate, 1,4 butane diol dimethacrylate, 1,6-hexane diol acrylate, 1,6 hexane diol methacrylate, octane diol diacrylate, octane diol dimethacrylate, decane diol diacrylate, decane diol dimethacrylate, trimethylol propane diacrylate, trimethylol propane dimethacrylate, trimethylol propane triacrylate, trimethylol propane trimethacrylate, pentaerythritol diacrylate, pentaerythritol dimethacrylate, pentaerythritol triacrylate, pentarythritol trimethacrylate, pentaerythritol tetra acrylate, pentaerythritol tetramethacrylate, dipentaerythritol diacrylate, dipentaerythritol dimethacrylate, dipentaerythritol triacrylate, dipentaerythritol trimethacrylate, dipentaerythritol tetramethacrylate, dipentaerythritol tetra acrylate, N,N'-methylene bis acrylamide, N,N'-methylene bismethacrylamide, trialyl isocyanurate, trialylamine, and tetraalyloxy ethane, and ester compounds of such a polyhydric alcohol as hydroquinone, catechol, resorcinol, and sorbitol with acrylic acid or methacrylic acid may be used. These cross-linking monomers may be used either singly or in the form of a mixture of two or more members.

As used herein, "polymer foams" are materials made by generating void spaces inside a bulk polymer, resulting in substantially reduced density. They can be open-celled or closed-celled. The nature of these cells and the cell size determine many properties of the polymer. For example, light weight and low thermal conductivity are the typical properties of a conventional foam. The density of conventional polystyrene foam is in the range of 0.02–0.2 g/cc with closed cells between 50–100 μm in diameter.

As used herein, "noncompressive drying" refers to drying methods for drying the materials, such as foams and cellulosic webs, that do not involve compressive nips or other steps causing significant densification or compression of a portion of the web during the drying process. Such methods include through-air drying; air jet impingement drying; non-contacting drying such as air flotation drying, through-flow or impingement of superheated steam; microwave drying and other radio frequency or dielectric drying methods; water extraction by supercritical fluids; water extraction by nonaqueous, low surface tension fluids; infrared drying; electronic beam irradiation; ultrasound; gamma radiation; applying a gas pressure differential; ultraviolet or visible light and other methods.

"Cell Pore Size" and "Cell Wall Thickness" are measures of the characteristic size of a cell in a foam and of the thickness of the wall between adjoining cells, respectively. In making such measurements, a sample is cut by a sharp razor. The cut foam is attached to metal stubs using copper tape and imaged in an environmental scanning electron microscope using 12 kV beam voltage (model E-2020 from Electroscan Corporation of Wilmington, Mass. or a similar instrument). The sample chamber pressure is about 1.2 Torr. The environmental backscatter electron detector is used to collect images, having the advantage of being able to discern any variations in composition. Magnification varies depending on the scale of the subject sample, with a 150 magnification being preferred for a general survey of the sample and a 2500 magnification to measure cell wall thickness and cell size. Cell wall thickness and cell size measurements are taken directly on the environmental scanning electron microscope. Manual measurement of cell wall thickness measurement is used. The cell wall thickness and cell size of each sample are averaged from at least 20 measurements.

"Water retention value", (WRV) is a measure that can be used to characterize some fibers useful for purposes of this invention. WRV is measured by dispersing 0.5 gram of fibers in deionized water, soaking overnight, then centrifuging the fibers in a 1.9 inch diameter tube with a 100 mesh screen at the bottom at 1000 G for 20 minutes. The samples are weighed, then dried at 105° C. for two hours and then weighed again. WRV is (wet weight–dry weight)/dry weight. Fibers useful for purposes of this invention can have a WRV of about 0.7 or greater, more specifically from about 1 to about 2. High yield pulp fibers typically have a WRV of about 1 or greater.

As used herein, "Absorbent Capacity" refers to the amount of distilled water that an initially 1-inch cube of absorbent fibrous material can absorb while in contact with a pool of room-temperature water and still retain after being removed from contact with the pool of liquid water and held on a metal screen and allowed to drip for 30 seconds. Absorbent capacity is expressed as grams of water held per gram of dry fiber. The structures of the present invention have absorbent capacity values of about 5 g/g or greater, preferably about 7 g/g or greater, more preferably from about 8 g/g to about 15 g/g, and most preferably about 9 g/g or greater.

As used herein, "bulk" and "density," unless otherwise specified, are based on oven-dry mass of a sample and a thickness measurement made at a load of 0.05 psi with a three-inch diameter circular platen. Thickness measurements of samples are made in a Technical Association of the Pulp and Paper Industries, Atlanta, Ga., (TAPPI) conditioned room (50% RH and 73° F.) after conditioning for at least four hours. Samples should be essentially flat and uniform under the area of the contacting platen. Bulk is expressed as volume per mass of fiber in cc/g and density is the inverse, g/cc. The bulk of the I-HIPE foams of the present invention may be about 6 cc/g or greater or about 10 cc or greater, such as from about 10 cc/g to about 200 cc/g, more specifically from about 20 cc/g to about 200 cc/g, and most specifically from about 15 cc/g to about 100 cc/g.

As used herein, "Wet Bulk" is based on a caliper measurement of a sample according to the definition of "bulk" above (at 0.05 psi), except that the conditioned sample is uniformly misted with deionized water until the moistened mass of the sample is approximately 250% of the dry mass of the sample (i.e., the added mass of the moisture is 150% of the dry sample weight). If the sample cannot absorb and retain enough moisture from misting to increase the mass by 150%, then the highest level of achievable moisture add-on below 150% but still above 100% moisture add on should be used. The Wet Bulk is calculated as the thickness of the substantially planar moistened sample under a load of 0.05 psi divided by the oven-dry sample basis weight in g/cc. Some embodiments of foams of the present invention can have a Wet Bulk of about 6 cc/g or greater, more specifically about 8 cc/g or greater, more specifically still about 10 cc/g or greater, more specifically still about 15 cc/g or greater, and most specifically about 20 cc/g or greater, with an exemplary range of from about 13 cc/g to about 35 cc/g.

As used herein, a material will be considered to be "water soluble" when it substantially dissolves in excess water to form a solution, thereby losing its initial form and becoming essentially molecularly dispersed throughout the water solution. As a general rule, a water-soluble material will be free from a substantial degree of cross-linking, as cross-linking tends to render a material water insoluble. A material that is "water insoluble" is one that is not water soluble according to the above definition.

As used herein, the term "water-swellable, water-insoluble" is meant to refer to a material that, when exposed to an excess of water, swells to its equilibrium volume but does not dissolve into the water. As such, a water-swellable, water-insoluble material generally retains its original identity or physical structure, but in a highly expanded state, during the absorption of the water and, thus, must have sufficient physical integrity to resist flow and fusion with neighboring materials.

As used herein, the term "solvent" is intended to represent a substance, particularly in a liquid form, that is capable of dissolving a material such as polymerizable monomers, reducing initiators, oxidizing initiators, crosslinkers, and surfactants used herein to form a substantially uniformly dispersed mixture at the molecular level. For freeze-drying embodiments, the solvent used in the mixture of fibers undergoing sublimation, wherein the solvent passes directly from its frozen state to a vapor state. As such, the solvent should have a freezing point at which the solvent changes from a liquid to a solid.

As used herein, a "portion" of an element represents any non-zero fraction of that element including all of the element. Thus, a portion of the removable phase could be, by way of example, 1%, 5%, 10%, 50%, 90%, or 100% of the removable phase. A portion of a composition having multiple elements could include differing fractions for each element. Thus, by Way of example, a portion of a structuring composition comprising surfactant, wet strength resin, starch, and water could be a mixture containing varying amounts of all four ingredients or could be a mixture of just a subset of the ingredients, such as starch, water, and surfactant.

Super critical fluids, as used herein, include solvents with a critical temperature of less than 200° C. including, but not limited to, carbon dioxide, diethyl ether, methyl chloride, trimethylamine, chlorpentafluoroacetone, perfluoroacetone, 1,1,2,2-tetrafluoroethane (R134), ethyl chloride, ethyl fluoride, methyl formate and acetaldehyde. Gases can be transformed to super critical fluids by either an elevated pressure or heating of the gas so that at least a portion of the gas condenses. The super critical pressure typically ranges from about 6,900 to about 69,000 kPa.

In the present invention, in-situ redux monomers coupled with supercritical fluid-assisted HIPE or I-HIPE preparation methods can result in a variety of advantages for foam-bases materials and articles and can be applied to the traditional formation of high internal phase ratio emulsions (HIPE) or I-HIPE to create super absorbent foams that exhibit improved fluid intake rate and/or fluid intake of multiple insults over the life of the composite, often without the problems associated with known absorbent composites.

HIPE Foams

Polymeric foams made using High-Internal-Phase-Ratio Emulsions (HIPE) technology are disclosed in U.S. Pat. No. 5,652,194, wherein collapsed polymeric foam materials can be prepared by polymerizing a particular type of water-in-oil emulsion. Related HIPE foams are also disclosed in U.S. Pat. No. 5,260,345; U.S. Pat. No. 5,817,704; and U.S. Pat. No. 5,268,224. Further relevant examples of foams are disclosed by F. A. Shutov in "Syntactic Polymer Foams" in Handbook of Polymeric Foams and Foam Technology, ed. D. Klempner and K. C. Frisch, Hanser Publ., New York, 1991, pp. 355 to 359. All of the foregoing references are herein incorporated by reference. In the present invention, the oil phase may comprise a super critical fluid or a blend of a supercritical fluid and other fluids such as liquid oils.

The oil phase of such HIPE emulsions may additionally comprise from about 67% to about 98% by weight of a monomer component having: (a) from about 5 to about 40% by weight of a substantially water-insoluble, monofunctional glassy monomer; (b) from about 30% to about 80% by weight of a substantially water-insoluble, monofunctional rubbery co-monomer; and (c) from about 10% to about 40% by weight of a substantially water-insoluble polyfunctional crosslinking agent component. The oil phase further can comprise from about 2% to about 33% by weight of an emulsifier component that is soluble in the oil phase and will provide a stable emulsion for polymerization. The water or "internal" phase of these HIPE emulsions comprises an aqueous solution containing from about 0.2% to about 20% by weight of a water-soluble electrolyte. The weight ratio of the water phase to the oil phase in these HIPE emulsions can range from about 12:1 to about 100:1. The polymerized foam is subsequently dewatered (with or without prior washing/treatment steps) to provide the collapsed foam material. The emulsion formation and polymerization steps are performed so that coalescence of the relatively small water droplets formed in the HIPE emulsion is reduced. This leads to an average cell size in the resulting polymeric foam material of about 50 microns or less. This reduction in coalescence can be consistently achieved by the use of certain emulsifier systems, by the use of lower temperatures during polymerization (curing), or both, as described hereafter. Moreover, these thin, collapsed absorbent polymeric foam materials can be consistently manufactured according to the process of the present invention on a potentially commercial scale, and at a potentially reasonable or low cost.

I-HIPE Foams

I-HIPE technology is disclosed in U.S. Provisional Patent Application No. 10/289,234, filed Nov. 6, 2002, herein incorporated by reference in its entirety. The chemical nature, makeup and morphology of the polymer material which forms the inverse HIPE foam structures of the present invention is determined by the types and quantity of the monomers, co-monomers and crosslinkers utilized in the emulsion. The methods of the present invention comprise inverse HIPE polymerization of in-situ redox monomers of superabsorbent polymer (SAP) with super-critical fluids, wherein the super-critical fluids either partially or completely replace the oil phase.

The inverse high internal phase emulsion is prepared by dispersing an oil phase in a water phase. The oil phase thus forms the dispersed droplets surrounded by the continuous, monomer containing water phase. The water phase contains an in-situ SAP precursor monomer solution and either a water-soluble oxidizing initiator or a water-soluble reducing initiator, but generally not both initiators (disregarding ineffective trace concentrations). When the water phase contains a water-soluble oxidizing initiator, then the oil phase contains an effective amount of an oil-soluble reducing agent, and vice versa. In some embodiments, an emulsifier is added to either the water phase or the oil phase. In-situ redox SAP polymerization proceeds in the water phase initiator upon contact with the counter-oxidizing initiator in the oil phase. In some embodiments, polymerizable monomers can be added to the oil phase. The weight ratio of the water phase to the oil phase in these inverse HIPE emulsions may range from about 2:1 to about 200:1, more specifically from about 3:1 to about 200:1, more specifically still from about 4:1 to about 200:1, and most specifically from about 5:1 to about 50:1.

Though the stated ingredients in the oil phase may have an inherently oil-like characteristic requiring no additional oil as a carrier, an oil carrier may be used which may then be removed from the foam after or during polymerization. The oil carrier can be the primary component of the oil phase (e.g., comprising about 90 weight % or greater of the oil phase, or about 60 weight % or greater), or can comprise less than 50 weight percent of the oil phase, such as from about 10 weight % to about 40 weight % of the oil phase. The oil phase can also comprise droplets of an aqueous solution suspended in the oil phase (a water-in-oil microemulsion, for example), or can comprise suspended particles such as the lipophilic particles of European Patent Application, EP 1,038,573-A2, published Sep. 27, 2000 by Shimida et al. herein incorporated by reference. An oil carrier for the oil phase can comprise a silicone oil, such as the silicone oils of U.S. Pat. No. 5,443,760, herein incorporated by reference; a mineral oil; a petrolatum extract; a vegetable oil; an animal fat; an organic solvent; or any combination thereof. Examples of oils that may be used for the present invention include almond oil, apricot kernel oil, avocado oil, cacao butter (theobroma oil), carrot seed oil, castor oil, citrus seed oil, coconut oil, corn oil, cottonseed oil, cucumber oil, egg oil, jojoba oil, lanolin oil, linseed oil, mineral oil, mink oil, olive oil, palm oil, kernel oil, peach kernel oil, peanut oil, rapeseed oil, safflower oil, sesame oil, shark liver oil, soybean oil, sunflower seed oil, sweet almond oil, tallow (beef) oil, tallow (mutton) oil, turtle oil, vegetable oil, whale oil, and wheat germ oil; alkanes generally containing at least six or at least ten or more carbon atoms such as cyclohexane, n-hexane, decane or hexadecane; aromatic hydrocarbons such as toluene; fluorinated hydrocarbons such as perfluorocyclohexane, perfluorohexane, perfluorododecane, and perfluoropolyethylene oxide; esters such as isopropyl laurate, isopropyl palmitate, hexyl laurate, isopropyl myristate, myristyl myristate, cetyl myristate, 2-octyldecyl myristate, isopropyl palmitate, 2-ethylhexyl palmitate, butyl stearate, decyl oleate, and 2-octyldodecyl oleate; glycol ester oils such as polypropylene glycol monooleate and neopentyl glycol 2-ethylhexanoate; polyhydric alcohol ester oils such as isostearate triglyceride and cocofatty acid triglycerides; squalane, squalene, waxes, styrene, divinylbenzene, butyl acrylate, 2-ethylhexyl acrylate, cyclohexyl acrylate, decyl acrylate, lauryl acrylate, dodecenyl acrylate, myristyl acrylate, palmityl acrylate, hexadecenyl acrylate, stearyl acrylate, octadecenyl acrylate, behenyl acrylate, butyl methacrylate, 2-ethylhexyl methacrylate, cyclohexyl methacrylate, decyl methacrylate, lauryl methacrylate, dodecenyl methacrylate, myristyl methacrylate, palmityl methacrylate, hexadecenyl methacrylate, stearyl methacrylate, octadecenyl methacrylate, behenyl methacrylate, and silicone macromonomers,. The oil may be a composition having a linear or branched chain, it may be saturated or unsaturated, it may be naturally derived or synthetically produced, it may comprise a compound having silicon atoms or compounds free of silicon items, or it may be a hydrocarbon or fluorocarbon type of organic oil. A mixture of different oils may also be employed.

In one embodiment, the oil phase or the carrier oil of the oil phase has a solubility in water of not more than about 2 g per 100 g of water at 20° C., or more specifically not more than about 1 g per 100 g of water at 20° C.

When supercritical fluids are employed, all or a portion of the oil phase may be removed by depressurizing the system and allowing the formerly supercritical material to vent away. Whether or not supercritical fluids are employed, remaining components of the oil phase may be removed after polymerization, if desired, by any known method, including pressing the foam to extrude oil, capillary wicking of the oil into an oil-absorbent blotter, vacuum removal or removal driven by an air pressure differential, stripping with heated gas or steam, heating to volatilize the oil or to decrease oil viscosity for easier mechanical removal, washing with a solvent such as acetone or other volatile organic fluid or washing with an aqueous solution comprising a surfactant for removal of the oil phase, extraction with supercritical fluids such as supercritical carbon dioxide, and the like, or any combination thereof. Similar operations can be applied to remove any of the unpolymerized material (e.g., remaining water, emulsifier, initiators, surfactants, electrolytes, and the like) of the I-HIPE foam after polymerization of the superabsorbent precursor monomer(s) has occurred in the water phase. For example, water can be removed by air drying, by pressing and blotting, by air pressure differential across the I-HIPE foam, by heating, and the like, or any combination thereof. Water-soluble materials or unbound solids particles or lose fibers can be removed by any combination of washing with water, steam stripping, impinging with air jets, mechanical vibration, vacuum treatment, and the like.

In some embodiments, polymerizable monomers may be added to the oil phase. For example, rubbery monomers such as butadiene and other known monomers for rubbery materials may be used to provide flexibility of the I-HIPE foam.

Super Critical Fluid Foams

In some embodiments for making foams with the aid of super critical fluids, high pressure reactions may be carried out in which a reactor is charged with an aqueous solution of monomers, an initiator, a surfactant, and a cosurfactant before purging with the super critical fluid. The reactor is then pressurized with liquid super critical fluid and mixed to form the emulsion. The mixture is then cured. After cooling to room temperature, the super critical fluid is then vented and the polymeric foam is removed from the reactor.

In the super critical fluid I-HIPE and HIPE foams, either the water phase or oil phase or both may contain solid matter such as particles or fibers. The solid matter may be hydrophobic or hydrophilic. Exemplary hydrophilic solid particles include titanium oxide, silica, zeolite, barium sulfate, calcium carbonate, kaolin, iron oxides, and the like. Nonfibrous solids may have an average particle diameter of 0.05 μm to 50 μm, more specifically from about 0.1 μm to about 5 μm, and the concentration and size may be adjusted to maintain stability of the inverse HIPE emulsion, or electrolytes and pH may be adjusted to maintain emulsion stability in the presence of the particles, as needed.

U.S. Pat. No. 6,261,679 discloses a foam-structured fibrous material in which cellulosic fibers are blended with the emulsion prior to polymerization. The fibers may be dispersed in the continuous phase with a mixer or other method. Upon polymerization, the fibers are trapped in the foam structure. The fibers may help prevent collapse of the foam to maintain high bulk, or may improve fluid transport in the foam. Inverse HIPE foams and HIPE foams formed with and without fibers present are within the scope of the present invention. When the I-HIPE foam or HIPE foam comprises fibers dispersed within the foam, the fibers may comprise any values for the weight percent of the fibers relative to the mass of the polymerized material. The weight percents include, but are not limited to, 1%, 5%, 10%, 20%, 30%, 40%, 50%, 60%, 70%, 80%, 90%, and 95%, such as from about 5% to about 90%, or from about 20% to about 80%. The cellulose fibers or superabsorbent particles are described in U.S. Pat. No. 6,261,679 herein incorporated by reference. The fibers include all known cellulosic fibers or fiber mixes comprising cellulosic fibers such as any natural or synthetic cellulosic fibers including, but not limited to: nonwoody fibers, such as cotton, abaca, kenaf, sabai grass, flax, esparto grass, straw, jute hemp, and bagasse, milkweed floss fibers, and pineapple leaf fibers; and woody fibers such as those obtained from deciduous and coniferous trees, including softwood fibers, such as northern and southern softwood kraft fibers; hardwood fibers, such as eucalyptus, maple, birch, aspen, or the like. Woody fibers may be prepared in high-yield or low-yield forms and may be pulped in any known method, including kraft, sulfite, groundwood, TMP, RMP, CTMP, BCTMP, and other known pulping methods. If bleached, any known bleaching method may be used. Synthetic cellulose types of fiber include rayon in all its varieties and other fibers derived from viscose or chemically modified cellulose. Chemically treated natural cellulosic fibers may be used such as mercerized pulps, chemically stiffened or crosslinked fibers, sulfonated fibers, and the like.

According to the present invention, it is not necessary to collapse the foam-like structure after or during polymerization when paper fibers are present in the foam. Indeed, the randomly oriented fibers may resist collapse and help the high-bulk structure maintain its configuration when wetted, particularly if wet-resilient fibers such as chemically cross-linked fibers (e.g., cross-linked prior to incorporation into a foam-like structure) or high-yield fibers are used.

The I-HIPE and HIPE may be formed by combining the water and super critical fluid phases by mixing them using the mechanical means known in the art. For example, conventional stirring devices and mixing devices may be used. Stirring devices equipped with propeller type, paddle type, turbine type vanes, homomixers, line mixers, and pin mills may be used. Shear agitation is generally applied to the extent and for a time period necessary to form a stable emulsion from the combined water and oil phases. Such a process may be conducted in either batchwise or continuous fashion and is carried out under conditions suitable for forming an emulsion wherein the oil phase droplets are dispersed to such an extent that the resulting foam will have the required pore volume. Known ultrasonic means can also be,applied to emulsify the oil phase and water phase.

Compositions of the present invention may also comprise in-situ SAP precursor monomers in the water phase and oil-soluble monomers or co-monomers, such as rubbery monomers, in the oil phase. In some embodiments, the rubbery monomer will normally comprise from about 5 to about 50%, or from about 8 to about 25% by weight of the monomer component. Each phase comprises an oxidizing initiator or a reducing initiator, but not more than trace amounts of both (i.e., not both in sufficient amounts to substantially interfere with the polymerization process).

Examples of monomers in the water phase of the present invention include, but are not limited to acrylic acid partially neutralized with aqueous sodium hydrozide and ascorbic acid, carboxyl-group containing monomers such as monoethylenically unsaturated mono or polycarboxylic acid such as methacrylic acid, acrylic acid, maleic acid, fumaric acid, crotonic acid, sorbic acid, itaconic acid, and cinnamic acid; carboxylic acid anhydride group-containing monomers such as monoethylenically unsaturated polycarboxylic acid anhydrides; carboxylic acid salt-containing monomers such as water soluble salts, (e.g. alkali metal salts, ammonium salts, amine salts), of monoethylenically unsaturated mono or polycarboxylic acids; sulfonic acid group containing monomers such as aliphatic or aromatic vinyl sulfonic acids, methacrylic and acrylic sulfonic acids; sulfonic acid salt group containing monomers such as alkali metal salts, ammonium salts, amine salts of sulfonic acid group containing monomers; hydroxyl group containing monomers such as monoethylenically unsaturated alcohols, monoethylenically unsaturated ethers or esters of polyols; amide group containing monomers such as vinylformamide, methacryl amides, acrylamides, N-hydroxyalkyl methacrylamides, N-hydroxy methacrylamides, hydroxypropyl methacrylate, hydroxypropyl acrylate, triethylene glycol methacrylate, triethyleneglycol acrylate, poly oxyethylene glycol mono allyl ether, polyoxyethylene glycol monoallyl ether, polyoxypropylene glycol mono methallyl ether, and polyoxypropylene glycol mono allyl ether; amide group containing monomers such as vinylformamide, methacrylamide, acrylamide, N-alkylamides, N-methalkylamides, N-hydroxyalkyl methacrylamides, N-hydroxyalkyl acrylamides, N,N-dihydroxyalkyl methacrylamides, N,N-dihydroxyalkyl acrylamides, vinyl lactams; amino group containing monomers such as amino group containing esters of monoethylenically unsaturated mono or di carboxylic acids, heterocyclic vinyl compounds, and quaternary ammonium salt group containing monomers such as N,N,N,-trialkyl-N-methacryloyloxyalkylammonium salts, and N,N,N,-trialkyl-N-acryloyloxyalkyl-ammonium salts. The oil phase of the present invention may comprise hydrogen peroxide dispersed in silicone oil. If necessary, diglycerol monooleate and sorbitan oleate may be added to either the water phase or the oil phase as an emulsifier to stabilize the inverse HIPE or HIPE foams.

The water soluble oxidizing initiator may be persulfates such as potassium persulfate, sodium persulfate, and ammonium persulfate; and peroxides such as hydrogen peroxide, potassium peracetate, sodium peracetate, potassium percabonate, sodium percabonate, and t-butuyl hydroxyperoxide. The oil soluble oxidizing initiator may be such peroxides as cumene hydroperoxide, t-butylhydroperoxide, di-t-butyl peroxide, diisoprapyl benzene hydroperoxide, p-menthane hydroperoxide, 1,1,3,3-tetramethylbutyl hydroperoxide, 2,5-dimethylhexane-2,5-dihydoperoside, benzoyl peroxide, and methylethyl ketone peroxide.

The water phase of the I-HIPE or HIPE comprises from about 20% to about 80% by weight of a monomer component, from about 0.01% to about 5% of a cross-linking agent, and from about 1% to 10% of a water-soluble oxidizing initiator or from about 1% to 10% of a water-soluble reducing initiator, and from about 0.01% to about 5% of an emulsifier component. The water phase further comprises electrolytes such as calcium chloride from about 0.1% to 5%. And the oil phase comprises from about 1% to 10% of an oil-soluble reducing initiator or from about 1% to 10% of an oil-soluble oxidizing initiator, and from about 0.01% to about 5% of an emulsifier component. The oil phase may comprise 5% to about 50% by weight of a monomer component by weight of a rubbery co-monomer; (c) from about 10% to about 40% of a cross-linking agent and (d) from about 0.01% to about 5% of an emulsifier component that is soluble in the oil phase.

A variety of polyethers, fluorochemicals (e.g., surfactants based on poly(hexafluoropropylene oxide) or perfluoropolyethers), and siloxanes are known to be effective for forming emulsions with water and supercritical $CO_2$. General principles on the selection, design, and use of surfactants in supercritical emulsions are disclosed by K. P. Johnston et al., "Microemulsions, Emulsions and Latexes," in Chemical Synthesis Using Supercritical Fluids, ed. P. G. Jessop, and W. Leitner (Weinheim, Germany: Wiley-VCH Verlag GmbH) 1999, pp. 127–146. Additional information on the use of several surfactants with supercritical $CO_2$ are disclosed by A. V. Yazdi et al., "Highly Carbon Dioxide Soluble Surfactants, Dispersants and Chelating Agents," Fluid Phase Equilibria, Vol. 117, Nos. 1–2, 1996, pp. 297–303.

For example, perfluoropolyether ammonium carboxylate surfactants in supercritical $CO_2$ emulsions were reported by C. T. Lee et al., "Water-in-Carbon Dioxide Emulsions: Formation and Stability," Langmuir, Vol. 15, No. 20, 1999, pp. 6781–6791. Polyether surfactants are mentioned in the publication, "Supercritical Carbon Dioxide/Water Emulsion Found Effective for Remediating Metal Contaminants in Waste," available online as of Jul. 28, 2002 at http://www.lanl.gov/worldview/news/releases/archive/02-030.shtml.

Surfactants based on poly(hexafluoropropylene oxide) and dimethyl siloxane for use in supercritical $CO_2$ are discussed by T. A. Hoefling, "Design and Synthesis of Highly Carbon Dioxide-Soluble Surfactants and Chelating Agents," Fluid Phase Equilibria, Vol. 83, 1993, pp. 203–212. A wide variety of polyoxyalkylenes and other known surfactants can be of potential use, though optimization of molecular weight may be needed for any particular process. Non-fluorinated and/or non-siloxane surfactants can be used, including nonionic surfactants, as disclosed by Juncheng Liu, et al., "Formation of Water-in-$CO_2$ Microemulsions with Non-Fluorous Surfactant LS-54 and Solubilization of Biomacromolecules," Chemistry—A European Journal, Vol. 8, No. 2, 2002, pp. 1356–1360. In the latter case, the Dehypon LS-54 surfactant (Cognis, Inc., Cincinnati, Ohio), one of many fatty alcohol alkoxilates that can be used within the scope of the present invention, comprises four $CO_2$-philic groups (propylene oxide) and five hydrophilic groups (ethylene oxide), which may have contributed to its effectiveness, according to Liu et al.

Other surfactants have been demonstrated, including compositions comprising polyacrylamides, and the surfactant systems disclosed in U.S. Pat. No. 5,358,046. Further, U.S. Pat. No. 5,733,964, "Surfactants for Heterogeneous Processes in Liquid or Supercritical Carbon Dioxide," herein incorporated by reference, discloses heterogeneous polymer mixtures comprising a polymer in liquid or supercritical $CO_2$ stabilized by poly(propylene oxide) or poly (butylene oxide) surfactants. These surfactants are said to be well suited for stabilizing heterogeneous polymer mixtures formed by micronizing techniques and by compressed fluid antisolvent applications. In particular, a disclosed emulsion contained poly(2-ethylhexyl acrylate), and Pluronic 17R2 surfactant (BASF Corp., Mount Olive, N.J.).

Hybrid fluorocarbon/hydrocarbon surfactants can be used, such as the system described by K. Harrison et al., "Water-in-Carbon Dioxide Microemulsions with a Fluorocarbon-Hydrocarbon Hybrid Surfactant," Langmuir, Vol. 10, No. 10, 1994, pp. 3536–3541. The C7F15CH ($OSO3$—Na+)C7H15 surfactant solubilized substantial amounts of water, with the water-to-surfactant ratios in a single phase microemulsion as high as 32 at 25° C. and 231 bar. Dispersion polymerization of methyl methacrylate in supercritical $CO_2$ was stabilized by poly(dimethylsiloxane) monomethacrylate (PDMS-mMA) in work reported by Mark L O'Neill, et al., "Dispersion Polymerization in Supercritical $CO_2$ with Siloxane-Based Macromonomer. 2. The Particle Formation Regime," Macromolecules, Vol. 31, No. 9, 1998, pp. 2848–2856.

Poly(1,1-dihydroperfluorooctyl acrylate) as a surfactant for supercritical $CO_2$ is disclosed by Mark L. O'Neill, et al., "Polymer Stabilized Emulsions in Supercritical Carbon Dioxide," Polym. Mater. Sci. Eng., Vol. 74, 1996, pp. 228–229. Another potentially useful surfactant is disclosed by Junchen Liu et al., "Investigation of Nonionic Surfactant Dynol-604 Based Reverse Microemulsions Formed in Supercritical Carbon Dioxide," Langmuir, Vol. 17, No. 26, 2001, pp. 8040–8043. The Dynol-604 surfactant (Air Products and Chemicals, Inc., Allentown, Pa.) is apparently free of fluorine and siloxane groups. A fluorinated sulfosuccinate compound was used as an emulsion stabilizer in work of X. Dong et al., "Phase Behavior and Micelle Size of an Aqueous Microdispersion in Supercritical $CO_2$ with a Novel Surfactant," Industrial & Engineering Chemistry Research, Vol. 41, No. 5, 2002, pp. 1038–1042.

Surfactants can be nonionic, anionic, or cationic, and can be fluorinated or free of fluorine, can contain siloxane groups or be free of siloxane groups, and can have molecular weights in any of the following ranges: 500 to 500,000; 1,000 to 1,000,000; 10,000 to 500,000; 20,000 to 2,000,000; about 5,000 or greater; about 50,000 or greater; about 500,000 or greater; less than 100,000; less than 65,000; less than 20,000; and from 500,000 to 5,000,000.

The small pores of the resulting structure can be combined with fibrous absorbent material and adapted for use in an absorbent article.

For example, a hydrophilic absorbent layer suitable for use in an absorbent article such as a sanitary napkin can be produced by SCF processing of a HIPE or I-HIPE polymer. Polyvinyl alcohol (PVA) can be crosslinked into a HIPE or I-HIPE foam using the procedure of Butler et al. in which polyfluoroether surfactants are used to stabilize an emulsion initially comprising an aqueous solution of acrylamide monomer (40% by weight), an initiator (K2S2O8, 2% by weight relative to the monomer), and a cosurfactant. The system is purged with $CO_2$ and then pressurized with liquid $CO_2$ and stirred to form an emulsion, then heated to reaction temperature (about 60° C.).

Antimicrobial or odor control properties can also be added. For example, metallic compounds such as copper hydroxide and zinc hydroxide may be used for this purpose. In addition, activated carbon or polysaccharide may also be used. The super critical fluid can also be used to impregnate the polymeric matrix with a plasticizer during or after initial production to increase the flexibility of the foam.

The resulting polymerized dispersion may be in the form of a porous solidified structure which is an aggregate of cells, the boundaries or walls of which cells comprise solid polymerized material. The cells themselves contain the relatively monomer-free liquid which, prior to polymerization, had formed the droplets in the liquid dispersion. The polymeric foams may be relatively closed-celled or relatively open-celled in character, depending on the polymeric material. Preferably, the foams are more open-celled.

The method of curing the resulting foam depends on the monomer and other makeup of the super critical fluid and water phases of the emulsion, the emulsifier system and the type and amounts of polymerization initiators utilized. In some embodiments, the curing conditions comprise maintenance of the emulsion at elevated temperatures above 100° C. for a time period ranging from about 1 to 72 hours. Alternatively, the emulsion may be cured at any of the following temperature ranges: from about 100° C. to about 200° C., from about 130° C. to about 200° C., from about 130° C. to about 180° C., from about 150° C. to about 175° C., greater than 190° C., from about 200° C. to about 270° C., less than about 170° C., and less than 130° C. Further, curing times can be any of the following: from about 1 hour to 24 hours, from about 1 hour to 3 hours, less than 2 hours, less than 1 hour, less than 30 minutes, less than 10 minutes, less than 1 minute, less than 30 seconds, from about 15 seconds to about 20 minutes, from about 1 minute to about 30 minutes, and from about 10 seconds to about 1 minute. Heating of the materials can be achieved by heated air in a convection oven or furnace, infrared radiation, electromagnetic radiation such as microwave or radiofrequency heating, contact heating with a heated object such as a metal or ceramic surface, induction heating, ultrasonic heating, laser heating, and the like. Curing can also be achieved by application of an electronic beam, ultrasonic radiation, ultraviolet light, gamma radiation, other electromagnetic radiation (e.g., 2.45 GHz RF energy or other RF energy at a frequency greater than 100 kHz, specifically greater than 5 MHz, and most specifically greater than 100 MHz), and the like.

After polymerization, the I-HIPE foam or HIPE foam material may be molded into any desired shape. These shapes include shapes adapted to conform with any part of the human body, including shapes suitable for good body fit and comfort in feminine care articles, diapers, and incontinence articles, such as the shapes disclosed in commonly owned U.S. Pat. Ser. No. 09/680,719, "Absorbent Articles with Molded Cellulosic Webs," filed Oct. 13, 2000 by Chen et al., and herein incorporated by reference. Molding can be achieved by a wide variety of methods, such as curing the I-HIPE foam or HIPE foam in a molded container, by mechanically pressing the foam after curing against a molded surface and optionally applying heat or plasticizers to increase the conformance of the foam; removing portions of the foam to create a sculpted foam structure (methods to remove portions of the foam can include cutting, laser ablation or laser drilling, ultrasonic ablation, mechanical abrasion, piercing, and so forth), and the like.

As used herein and in the appended claims, the singular forms "a," "an," and "the" include plural reference unless the context clearly indicates otherwise. Thus, for example, reference to a "compound" is a reference to one or more such compounds and includes equivalents thereof known to those skilled in the art, and so forth.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

Test Methods for Absorbent Properties

1. Absorbency Under Load

"Absorbency Under Load" (AUL) is a measure of the liquid retention capacity of a material under a mechanical load. It is determined by a test which measures the amount in grams of an aqueous solution, containing 0.9 weight percent sodium chloride, a gram of a material can absorb in 1 hour under an applied load or restraining force of about 0.3 pound per square inch.

The AUL apparatus comprises a Demand Absorbency Tester (DAT) as described in U.S. Pat. No. 5,147,343, issued Sep. 15, 1992 to Kellenberger, herein incorporated by reference, which is similar to a GATS (Gravimetric Absorbency Test System), available from M/K Systems, Danners, Mass. A level porous plate is used having ports confined within a 2.5 cm. diameter area to provide liquid saline solution, 0.9 (w/w) % NaCl, delivered from a reservoir to the porous plate such that there is no hydraulic head (neither positive pressure nor suction) at the top of the porous plate. Thus, fluid may be absorbed into the absorbent without overcoming a significant capillary pressure barrier to move liquid out of the porous plate. Fluid absorbed from the plate is replaced with liquid from the reservoir, which resides on an electronic balance that measures the amount of liquid removed from the reservoir and absorbed into the absorbent. The sample on the porous plate resides within a section of one-inch (2.54 cm) inside diameter thermoplastic tubing machined-out slightly to be sure of concentricity. 100 mesh stainless steel wire cloth is fused on the bottom of the cylinder to restrain the sample and any particulates therein. Care must be taken to maintain a flat smooth bottom and not distort the inside of the cylinder. A 4.4 g piston is made from one inch diameter solid material (e.g., Plexiglas) and is machined to closely fit without binding in the cylinder. A standard 100 g weight placed on the piston is used to provide a 21,000 dyne/sq. cm. (about 0.3 psi) restraining load which is commonly experienced in infant diapers. To carry out the test with a foam-like fibrous material or a foam, a material sample is cut into circular discs with a diameter slightly smaller than one inch to freely fit within the sample tube. The sample mass should be from about 0.08 g to 0.18 g.

This test is initiated by placing a 3 cm diameter GF/A glass filter paper onto the porous plate (the paper is sized to be larger than the inner diameter and smaller than the outer diameter of the cylinder), to insure good contact while eliminating evaporation over the ports of the DAT and then allowing saturation to occur. The material to be tested is placed on the wire cloth at the bottom of the AUL apparatus. The sample is then covered with a plastic spacer disc, weighing 4.4 grams and having a diameter of about 0.995 inch, which serves to protect the sample from being disturbed during the test and also to uniformly apply a load on the entire sample. After carefully placing the piston and weight on the sample in the cylinder, the AUL apparatus is placed on the glass filter paper. The amount of fluid pick-up is monitored as a function of time either directly by hand, with a strip chart recorder or directly into a data acquisition system.

The amount of fluid pickup measured after one hour is the AUL value, expressed as grams of liquid per dry gram of the tested material.

The AUL may be a function of the oil-to-water ratio of the inverse HIPE foam. Generally, a higher oil-to-water ratio will result in a higher void volume in the foam which may result in a higher AUL. For the materials of the present invention, the AUL value may be, for example, from about 10 grams/gram to 200 grams/gram, more specifically from about 20 grams/gram to 50 grams/gram, and most specifically from about 25 grams/gram to 40 grams/gram. In other embodiments, the AUL of the materials of the present invention is above 6 grams/gram, more specifically about 5 grams/gram or greater, with an exemplary range of from about 9 to about 40 grams/gram 2. Free Swell Capacity The Free Swell capacity test measures the amount in grams of an aqueous solution, containing 0.9 weight percent sodium chloride, that a gram of a material can absorb in 1 hour under negligible applied load. The test is done as described above for the AUL test, except that the 100 gm weight is not placed on the sample. For the materials of the present invention, the Free Swell Capacity may be, for example, from about 5 to 150, more specifically from about 10 to 50, and most specifically from about 12 to 30.

3. Absorbent Capacity

As used herein, "Absorbent Capacity" refers to the amount of distilled water that an initially 1-inch cube of absorbent fibrous material can absorb while in contact with a pool of room-temperature water and still retain after being removed from contact with the pool of liquid water and held on a metal screen and allowed to drip for 30 seconds. Absorbent capacity is expressed as grams of water held per gram of dry fiber. The structures of the present invention have absorbent capacity values of about 5 g/g or greater, preferably about 7 g/g or greater, more preferably from about 8 g/g to about 15 g/g, and most preferably about 9 g/g or greater, with exemplary ranges of from about 5 g/g to 20 g/g. or from about 10 g/g to 40 g/g.

4. Free Swell:AUL Ratio

As used herein, "Free Swell:AUL Ratio" is the ratio of Free Swell Capacity to AUL. It will generally be greater than one. The higher the value, the more sensitive the material is to compressive load, meaning that the sample is less able to maintain its potential pore volume and capillary suction potential under load. Desirably, the materials of the present invention have "Free Swell:AUL Ratio" f about 4 or less, more specifically about 2 or less, more specifically still about 1.5 or less, and more specifically about 1.3 or less, win an exemplary range of from about 1.2 to about 2.5.

We claim:

1. A method of making an absorbent foam comprising:
   a) combining a water phase and a super critical fluid phase, said water phase comprising effective amounts of at least one superabsorbent precursor monomer; and
   b) combining an oxidizing initiator in one of the super critical fluid phase and water phase, and a reducing initiator in the other of the supercritical fluid phase and water phase, whereby the super critical fluid phase and the water phase form an emulsion, such that polymerization of the at least one superabsorbent precursor monomer takes place in the water phase to form a polymerized material.

2. The method of claim 1, wherein the super critical fluid phase contains an oxidizing initiator and the water phase contains a reducing initiator.

3. The method of claim 1, wherein the super critical fluid phase contains a reducing initiator and the water phase contains an oxidizing initiator.

4. The method of claim 1, further comprising a chemical crosslinker in at least one of the super critical fluid phase and water phase.

5. The method of claim 4, wherein the polymerized material is cured so that the chemical crosslinker crosslinks the polymerized material.

6. The method of claim 4, wherein curing the polymerized material comprises heating the polymerized material to a temperature of at least about 100° C.

7. The method of claim 4, wherein curing the polymerized material comprises applying energy in the form of at least one of radiofrequency radiation, ultrasound, an electron beam, gamma radiation, and ultraviolet or visible light.

8. The method of claim 1, further comprising an oil phase.

9. The method of claim 1, further comprising providing an electrolyte in the water phase.

10. The method of claim 9, wherein the electrolyte is selected from alkali metal salts, ammonium salts, amine salts, and salts of carboxylic acids.

11. The method of claim 1, wherein at least a portion of the unpolymerized material comprising an unreacted portion of the super critical fluid phase is removed.

12. The method of claim 1, wherein at least a portion of the unpolymerized material comprises an unreacted portion of the water phase is removed.

13. The method of claim 11, wherein removing at least a portion of the unpolymerized material comprises heating the unpolymerized material.

14. The method of claim 12, wherein removing at least a portion of the unpolymerized material comprises heating the unpolymerized material.

15. The method of claim 11, wherein removing at least a portion of the unpolymerized material comprises non-compressive drying of the polymerized material.

16. The method of claim 1, further comprising combining absorbent fibers with one of the water phase, the supercritical fluid phase, or the supercritical fluid-in-water emulsion.

17. The method of claim 16, wherein the absorbent fibers comprise cellulosic fibers.

18. The method of claim 1, further comprising combining insoluble particles with one of the water phase, the supercritical fluid phase, the water-in-super critical fluid phase or the super critical fluid-in-water emulsion.

19. The method of claim 1, further comprising molding the polymerized material to have a non-planar, three-dimensional shape.

20. The method of claim 1, wherein the at least one superabsorbent precursor monomer comprises a rubbery monomer.

21. The method of claim 1, wherein the at least one superabsorbent precursor monomer comprises an organic unsaturated carboxylic acid or salt thereof.

22. The method of claim 1, wherein the at least one superabsorbent precursor monomer comprises at least one of acrylic acid, methacrylic acid, maleic acid, itaconic acid, and salts thereof.

* * * * *